United States Patent [19]

Zeidler

[11] 4,006,173

[45] Feb. 1, 1977

[54] PROCESS FOR CONTINUOUS PREPARATION OF CARBOXYLIC ACIDS

[75] Inventor: Ulrich Zeidler, Dusseldorf-Benrath, Germany

[73] Assignee: Henkel & Cie G.m.b.H., Dusseldorf-Holthausen, Germany

[22] Filed: Mar. 21, 1974

[21] Appl. No.: 453,505

[30] Foreign Application Priority Data

Mar. 23, 1973 Germany ............... 2314454

[52] U.S. Cl. .............. 260/413; 260/524 R; 260/531 R; 260/537 P
[51] Int. Cl.² ............. C07C 51/24; C07C 51/33; C07C 55/02; C07C 57/00
[58] Field of Search .......... 260/413, 531 R, 524 R, 260/537 P

[56] References Cited

UNITED STATES PATENTS

| | | | |
|---|---|---|---|
| 3,711,523 | 1/1973 | Pultinas, Jr. et al. | 260/413 |
| 3,816,525 | 6/1974 | Schreyer et al. | 260/531 R |
| 3,855,257 | 12/1974 | Pultinas, Jr. | 260/413 |
| 3,865,856 | 2/1975 | Dohr et al. | 260/413 |

FOREIGN PATENTS OR APPLICATIONS

2,086,521  12/1971  France ............... 260/413

*Primary Examiner*—Winston A. Douglas
*Assistant Examiner*—P. E. Konopka
*Attorney, Agent, or Firm*—Hammond & Littell

[57] ABSTRACT

A process for producing carboxylic acids having at least 5 carbon atoms in which a mixture of vicinal diols having at least 6 carbon atoms with 0.01 to 0.5 mol per cent of heavy metal compound catalyst is continuously introduced, in an amount and at a rate such that the reaction is maintained, into an initiated mixture of vicinal diols having at least 6 carbon atoms, carboxylic acids formed therefrom and a heavy metal compound catalyst, which is contacted with an oxygen containing stream of gas, the reaction being carried out at temperatures between 40° C and 200° C, preferably 60° C to 140° C, and the oxidation mixture is continuously drawn off.

14 Claims, No Drawings

PROCESS FOR CONTINUOUS PREPARATION OF CARBOXYLIC ACIDS

THE PRIOR ART

Splitting of vicinal diols by oxidation with formation of carboxylic acids has been known for a long time. Equivalent amounts of lead tetraacetate, sodium metaperiodate and other compounds with atoms in high stages of oxidation are used as oxidizing agents. Owing to the fact that equivalent amounts of oxidizing agents have to be used, such a method is economically uninteresting.

A process is further known in which the oxidation of the vicinal diols is carried out with percarboxylic acids in the presence of ruthenium-III salts or cobalt-II salts. However, this discontinuously operating process does not prove satisfactory because of the use of equivalent amounts of percarboxylic acids.

A process for the oxidative cleavage of vicinal diols with oxygen containing gases in the presence of heavy metal compound catalysts and in the presence of aprotic polar solvents has not been found to be technically useful, since the use of such solvents makes the process unduly expensive.

Furthermore, a process for the preparation of carboxylic acids is known in which vicinal diols are brought in contact with an oxygen containing stream of gas at elevated temperature in the presence of a heavy metal compound catalyst and a high-boiling solvent, in which the water from the reaction and low-boiling oxidation products are removed from the reaction mixture by the stream of gas. The chief disadvantage of this process, besides the discontinuous operation thereof, is that relatively high additions of from 1 to 2 mol percent of the heavy metal compound catalyst based upon the diol used, were necessary for carrying out the reaction.

In a similar discontinuous process the amount of catalyst may indeed be reduced to 0.001 to 0.1 mol percent, but 20 to 30 mol percent of percarboxylic acid must be added at the same time. The one disadvantage common to all previously known processes for the splitting of diols is the use of a solvent.

OBJECTS OF THE INVENTION

It is an object of the present invention to provide a continuous process for the preparation of carboxylic acids having at least 5 carbon atoms by oxidative cleavage of vicinal diols having at least 6 carbon atoms, which to a great extent eliminates the above-mentioned disadvantages and is suitable for technical use.

It is another object of the present invention to provide a process for the continuous preparation of carboxylic acids by the catalytic oxidation of vicinal diols with oxygen containing gases in the presence of heavy metal catalysts.

It is a further object of the present invention to provide a process in which a mixture of the vicinal diols with 0.01 to 0.5 mol percent of heavy metal compound catalyst is continuously introduced, in an amount and at a rate such that the reaction is maintained, into an initiated mixture of vicinal diols having at least 6 carbon atoms, carboxylic acids formed therefrom and a heavy metal compound catalyst, which is contacted with an oxygen containing stream of gas, the reaction being carried out at temperatures between 40° C and 200° C, preferably 60° C to 140° C, and the oxidation mixture is continuously drawn off.

These and further objects of the present invention will become apparent as the description thereof proceeds.

DESCRIPTION OF THE INVENTION

The present invention relates to a process for the continuous preparation of carboxylic acids by the catalytic oxidation of vicinal diols with oxygen containing gases in the presence of heavy metal catalysts.

According to the present invention, a mixture of the vicinal diols having at least 6 carbon atoms with 0.01 to 0.5 mol percent of heavy metal compound catalyst is continuously introduced, in an amount and at a rate such that the reaction is maintained, into an initiated mixture of vicinal diols having at least 6 carbon atoms, carboxylic acids formed therefrom and a heavy metal compound catalyst, which is contacted with an oxygen containing stream of gas, the reaction being carried out at temperatures between 40° C and 200° C, preferably 60° C to 140° C, and the oxidation mixture is continuously drawn off.

More particularly, the present invention provides a process for the continuous production of carboxylic acids having at least 5 carbon atoms comprising (1) providing an initiated mixture consisting essentially of a vicinal diol having at least 6 carbon atoms, the carboxylic acids formed therefrom and a catalytic amount of a heavy metal compound catalyst into which an oxygen containing stream of gas is continuously introduced; (2) continuously introducing into said initiated mixture, a starting material mixture consisting essentially of a vicinal diol having at least 6 carbon atoms with 0.01 to 0.5 mol % of a heavy metal catalyst in such an amount and at such a rate that the reaction is maintained, the reaction being carried out at a predetermined temperature between 40° C and 200° C to produce an oxidation mixture; (3) continuously withdrawing said oxidation mixture at a rate substantially the same as the rate of introduction of said starting material mixture and (4) continuously recovering said carboxylic acids having at least 5 carbon atoms.

Preferably the invention is conducted in a multistage reactor such as a cascade reactor.

The process is applicable to terminal and non-terminal vicinal diols which may be both purely acyclic or may contain cycloalkyl or aryl groups. These diols may also be substituted if desired by hetero-atoms or hetero-atom groups, provided these are not themselves oxidizable under the reaction conditions such as halogen atoms, ether groups or ester groups. Preferably, the diols utilized have a total of 6 to 35 carbon atoms and have the formula

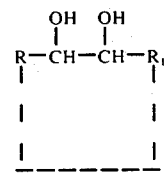

wherein R is a member selected from the group consisting of alkyl having from 4 to 33 carbon atoms and phenyl, $R_1$ is a member selected from the group consisting of hydrogen, alkyl having from 1 to 29 carbon atoms and phenyl, and R and $R_1$ when taken together are butylene. Examples of diols utilizable as starting substances include: hexanediol-1,2, heptanediol-1,2, octanediol-1,2, octanediol-2,3, octanediol-3,4, nonanediol-1,2, decanediol-1,2, decanediol-5,6, dodecanediol-6,7, tetradecanediol-7,8, hexadecanediol-8,9, octadecanediol-9,10, cyclohexanediol-1,2, 1,2-diphenyl-1,2-dihydroxyethane, 1-phenyl-1,2-dihydroxyethane.

Preferably vicinal diols having 6 to 18 carbon atoms and especially purely aliphatic diols are used in the process of the invention.

These diols may be used singly or in admixture with one another, i.e. in particular the diol mixtures obtained by hydroxylation of certain olefin fractions may also be used. Especially preferred as starting material are mixtures of nonterminal vicinal diols having 14 to 18 carbon atoms.

Suitable catalysts are salts, oxides, sulfides and complex compounds of transition metals, which can occur in at least two different positive valency stages and which can be converted by oxygen into a higher valency state, as is the case, for example manganese, cobalt, copper, cerium, vanadium and others, wherein cobalt-II compounds are preferred.

The preferred catalysts are cobalt-II salts and complexes which are soluble in the reaction mixture, for example salts of the said metals with higher fatty acids, such as salts of lauric, myristic or palmitic acid.

The reaction temperature is maintained below the boiling point temperature of aldehydes having at least 5 carbon atoms, such that these aldehydes will be maintained in the reaction mixture until converted into the final carboxylic acid product. However the shorter chain aldehydes may boil out of the solution and be entrained away by the gaseous stream of oxygen.

Thus the reaction is carried out at temperatures between 40° C and 200° C, preferably between 60° C and 140° C. If the reaction temperature is between 80° C and 120° C, it is especially preferred for carrying out the process without using a solvent.

The oxidation gas used may be air or other oxygen inert gas mixtures. Preferably pure oxygen, i.e. oxygen of commercial quality, which does not contain more than 10% by volume of other gases, is used as the oxidation gas.

The oxidation gases should be brought in contact with the diol to be oxidized in as finely divided state as possible. This may be effected by blowing in the gas through several fine jets at the bottom of the reaction vessel. A high-speed stirrer can also be introduced directly above the oxygen inlet at the bottom of the reaction vessel, or the stirrer itself may be provided with bores for the supply of oxidation gas.

When working in at high temperatures, and with relatively large amounts of reactants, it is advisable to preheat the oxidation gas to the temperature of the reaction mixture. The rate of introduction of the stream of oxidation gas is dependent upon the apparatus. In particular the type of feed of the gas and its distribution in the reaction mixture are of importance. The rate of introduction of the stream of oxidation gas also is dependent upon the total amount and rate of addition of the diol-catalyst mixture and on the working temperature.

For carrying out the continuous process of the invention, a multistage cascade apparatus composed of at least two and preferably several stages, with each stage being a bubble column reactor has proved to be advantageous. It is especially preferable to utilize a multistage apparatus with 2 to 4 stages. But any other apparatus which permits a continuous supply of a diol-catalyst mixture to an initiated mixture of diol, carboxylic acid and catalyst as well as a removal of the oxidation mixture, may also be used. For the start of the continuous process an initiated mixture of vicinal diol, carboxylic acids formed therefrom by oxidation and catalyst must first be prepared in the first cascade stage. This may be effected by one of the previously known processes, for example by introduction of the oxidizing agent gas into a mixture of vicinal diol with 2 mol percent of catalyst and a solvent to liquefy the mixture, which solvent may consist of a carboxylic acid or a polar or non-polar solvent. The preparation of the initial mixture in the first cascade stage, however, can also be carried out by oxidation with 0.1 mol percent of a heavy metal catalyst and 20 to 30 mol percent of percarboxylic acid. After various induction times, the oxidation starts and produces in the first cascade stage an already largely oxidized liquid material, to which the mixture of vicinal diol to be oxidized and 0.01 to 0.5 mol percent of catalyst can now be fed without further additions. In the now progressing continuous oxidation, the diol oxidate itself serves as solvent, so that a further addition of solvents in order to keep the reaction mixture liquid is un-necessary. The oxidation mixture formed in this continuous process is continuously fed into the second cascade stage, where it comes in contact with further oxidizing agent gas and goes from there into the next cascade stage, in which further oxidation may occur. The number of bubble column reactors required to make up the cascade apparatus, depends upon different reaction conditions, such as reaction temperature, oxidizing gas supply, diol feed, duration of the mixture in the individual cascade stages, distribution of the oxidizing gas in the diol oxidizing agent mixture and other factors. In general, however, a large number is not necessary if the reaction is carried out in the especially preferred temperature range of 80° C to 120° C, because a major amount of the oxidation can be obtained in the first cascade stage.

The speed at which the inactive, or unreacted, feed stock mixture of diol and preferably 0.1 mol percent of catalyst can be passed from a feed stock storage container into the initiated mixture of the first cascade stage is dependent on and limited by various factors such as reaction temperature, oxidizing gas supply, contamination of the starting materials by inhibitors. If the addition of the inactive diol-catalyst mixture is too rapid, the reaction stops, which immediately becomes noticeable by a drop in the reaction temperature. But also a very slow addition of inactive diol-catalyst mixture may lead to an interruption of the reaction. The addition of the inactive diol-catalyst mixture and the removal of the oxidation mixture has to be carried out at a speed such that the reaction always progresses evenly and does not fall off. A steady reaction temperature may be considered as an external indication that the reaction is progressing evenly. The reaction is advantageously carried out in the temperature range from 80° C to 120° C and the yield of carboxylic acid obtained ranges from 75% to 87% by weight based on the non-terminal diols used.

It is also possible to use solvents in the continuous process of the invention. To prevent the reaction from prematurely falling off it is in this case, however, necessary to a still greater extent than in the prior art discontinuous oxidation processes to use purified solvents containing only minimal amounts of substances capable of hampering the catalytic oxidation reaction. This is especially true at low working temperatures around 60° C.

The rate of supply of the oxidizing gas can also be altered in order to maintain a steady reaction rate.

As in the discontinuous process for the oxidation of vicinal diols in the presence of a heavy metal catalyst and a solvent by an oxygen containing stream of gas at temperatures between 40° C and 200° C, in the present process water and low-boiling oxidation products which are also found in the reaction are also removed from the reaction mixture with the gaseous stream.

The separation of the oxidation mixture may be effected by distillation or extraction of the carboxylic acids formed with aqueous-alkali solutions.

Advantages of the process according to the present invention are that carboxylic acids can be prepared in high yields and great purity. Furthermore since the diol, in contrast to the prior art discontinuous processes, is rapidly oxidized shortly after its addition to the reaction mixture, esterification reactions are avoided and the yields of the desired carboxylic acids are thereby increased. The by-products formed to a small extent during the reaction, for example carboxylic acid esters, are removed by known processes.

The following examples are merely illustrative of the present invention without being deemed limitative in any manner thereof.

EXAMPLE 1

The experiment was carried out in a cascade reactor consisting of three bubble column units with a total volume of about 150 ml. In the first cascade stage a stream of oxygen was introduced into an initiated mixture of non-terminal diols of chain lengths $C_{14}$ to $C_{18}$ with crude diol oxidate formed therefrom as solvent and 2 mol percent of cobalt-II laurate as catalyst. Solid diol mixed with 0.1 mol percent of cobalt-II laurate was continuously fed into this reactive mixture at a flow rate of 15 gm/hour and the oxidation mixture was correspondingly drawn off to the next cascade stage at the same flow rate of 15 gm/hr. The reaction temperature was 100° C. After a total reaction time of 5.5 hours the degree of reaction in the first and the third cascade stage amounted to 90% and 96%, respectively. The yield of obtained carboxylic acid was 79% of theory, referred to the diols used.

For this experiment a cascade reactor having four bubble column units with a total volume of about 200 ml was utilized. In the first cascade stage a stream of oxygen was introduced into the starting material, an active 10% solution of a mixture of nonterminal diols of chain lengths $C_{14}$ to $C_{18}$ in n-decanoic acid as solvent. An inactive 10% solution of non-terminal diols of chain lengths $C_{14}$ to $C_{18}$ in n-decanoic acid with 0.1 mol percent of cobalt-II laurate as catalyst was added continuously to this active solution at a reaction temperature of 60° C. Based upon a flow rate of addition of 95 ml/hour, the average residence time of the solution in the apparatus was 1.6 hours. The experiment was carried out for 32 hours, without any decrease in the activity being observed. After about 30 hours the degree of reaction in the four cascade stages was, respectively, 56%, 74%, 84% and 91%. The degree of reaction in the first reactor stage fluctuated between 50% and 57% during the period of the experiment. The total yield of carboxylic acid mixture of chain lengths $C_5$ to $C_9$ was 87% of theory, based on the diols used.

EXAMPLE 3

For this experiment a cascade reactor having two bubble column units with a total volume of about 100 ml was utilized. In the first cascade stage a stream of oxygen was introduced into the starting material, an active 10% solution of a mixture of non-terminal diols of chain lengths $C_{14}$ to $C_{18}$ in unpurified n-decanoic acid (commercials product) as solvent. An inactive solution of non-terminal diols of chain lengths $C_{14}$ to $C_{18}$ in unpurified n-decanoic acid containing 0.5 mol percent of cobalt-II laurate as the catalyst, was continuously added to this active solution at a reaction temperature of 100° C. Based upon an input flow rate of addition of 51 ml/hour the average residence time in the apparatus was 1.8 hours. The experiment was carried out for a total reaction time of 6.7 hours without any lessening of the activity being observed. Both after 3.5 hours and after 6.7 hours, the diol conversion amounted to 97% in the first stage and 98–99% in the second stage. The total yield of carboxylic acid mixture was 75% theory, based on the diols used.

The advantages of the continuous process according to the invention are that, compared with the previous discontinuous process, the reaction can be carried out with substantially smaller amounts of catalyst; approximately 0.1 mol percent compared with about 2 mol percent for the prior art. Furthermore it is also possible to carry out the oxidation without a solvent and prepare the carboxylic acids products in substantial yields. Because of this, the process is economically feasible, since the distillation of the solvent, which amounts to about 3 to 10 kg per kg of acid produced, is eliminated and thus a smaller capital investment is required and also cost of materials is less. Because of the continuous process according to the invention the vicinal diols which are readily obtainable from petro-chemical crude substances can now be used as raw materials for the synthesis of carboxylic acids in an economically feasible process.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

I claim:

1. A process for the continuous production of carboxylic acids having at least 5 carbon atoms comprising (1) providing an initiated mixture consisting essentially of (a) a vicinal diol having at least 6 carbon atoms, having the formula

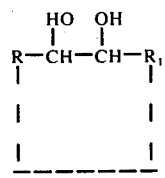

wherein R is selected from the group consisting of phenyl and alkyl having 4 to 33 carbon atoms, $R_1$ is selected from the group consisting of hydrogen, phenyl and alkyl having 1 to 29 carbon atoms, and R and $R_1$ when taken together are butylene; with the proviso that the total number of carbon atoms in said vicinal diol does not exceed 35 carbon atoms, (b) the carboxylic acids formed therefrom and (c) a catalytic amount of a heavy metal compound catalyst of soluble compounds of heavy transition metals which have two different oxidation states and which can be oxidized into the higher of said two states during the reaction, into which (d) an oxygen containing stream of gas is continuously introduced; (2) continuously introducing into said initiated mixture a starting material mixture consisting essentially of said vicinal diol having at least 6 carbon atoms with 0.01 to 0.5 mol % of said heavy metal catalyst in such an amount and at such a rate that the reaction is maintained, the reaction being carried out at a predetermined temperature between 40° C and 200° C to produce an oxidation mixture; (3) continuously withdrawing said oxidation mixture at a rate substantially the same as the rate of introduction of said starting material mixture and (4) continuously recovering said carboxylic acids having at least 5 carbon atoms.

2. The process of claim 1, in which said reaction of step (2) is carried out at a predetermined temperature between 80° C and 120° C.

3. The process of claim 1, in which said reaction of step (2) is carried out at a predetermined temperature between 60° C and 140° C.

4. The process of claim 1, in which said soluble heavy transition metal compounds are selected from the group consisting of cobalt-II salts and cobalt-II complexes.

5. The process of claim 1, in which the reaction of step (2) is carried out such that said predetermined temperature is maintained constant.

6. The process of claim 1, in which said vicinal diol is an aliphatic vicinal diol having 6 to 18 carbon atoms.

7. The process of claim 6, in which said vicinal diol is a mixture of non-terminal vicinal diols having 14 to 18 carbon atoms.

8. A process for the continuous production of carboxylic acids having at least 5 carbon atoms in a multistage reaction zone having at least two stages comprising (1) providing in a first stage of said reaction zone an initiated mixture consisting essentially of (a) a vicinal diol having at least 6 carbon atoms, having the formula

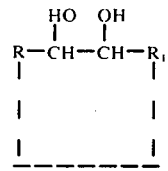

wherein R is selected from the group consisting of phenyl and alkyl having 4 to 33 carbon atoms; $R_1$ is selected from the group consisting of hydrogen, phenyl and alkyl having 1 to 29 carbon atoms, and R and $R_1$ when taken together are butylene; with the proviso that the total number of carbon atoms in said vicinal diol does not exceed 35 carbon atoms, (b) the carboxylic acids formed therefrom and (c) a catalytic amount of a heavy metal compound catalyst of soluble compounds of heavy transition metals which have two different oxidation states and which can be oxidized into the higher of said two states during the reaction, into which (d) an oxygen containing stream of gas is continuously introduced; (2) continuously introducing into said initiated mixture, in said first stage, a starting material mixture consisting essentially of said vicinal diol having at least 6 carbon atoms with 0.01 to 0.5 mol % of said heavy metal catalyst in such an amount and at such a rate that the reaction is maintained, the reaction being carried out at a predetermined temperature between 40° C and 200° C to produce an oxidation mixture; (3) continuously feeding said oxidation mixture into the next stage of said multistage zone into which an oxygen containing stream of gas is continuously introduced, at a rate substantially the same as the rate of introduction of said starting mixture, to mix with the reaction mixture within said next stage; (4) repeating step (3) if there are more than two stages; (5) continuously withdrawing said oxidation mixture at a rate substantially the same as the rate of introduction of said starting material mixture and (6) recovering said carboxylic acids having at least 5 carbon atoms.

9. The process of claim 8, in which said reaction of step (2) is carried out at a predetermined temperature between 80° C and 120° C.

10. The process of claim 9, in which said reaction of step (2) is carried out at a predetermined temperature between 60° C and 140° C.

11. The process of claim 8, in which said soluble heavy transition metal compounds are selected from the group consisting of cobalt-II salts and cobalt-II complexes.

12. The process of claim 8, in which the reaction of step (2) is carried out such that said predetermined temperature is maintained constant.

13. The process of claim 8, in which said vicinal diol is an aliphatic vicinal diol having 6 to 18 carbon atoms.

14. The process of claim 13, in which said vicinal diol is a mixture of non-terminal vicinal diols having 14 to 18 carbon atoms.

* * * * *